US008491936B2

(12) United States Patent
Rabiei et al.

(10) Patent No.: US 8,491,936 B2
(45) Date of Patent: Jul. 23, 2013

(54) FUNCTIONALLY GRADED BIOCOMPATIBLE COATING AND COATED IMPLANT

(75) Inventors: Afsaneh Rabiei, Raleigh, NC (US); Jerome J. Cuomo, Cary, NC (US); Brent C. Thomas, Lillington, NC (US)

(73) Assignee: North Carolina State University, Raleigh, NC (US)

( * ) Notice: Subject to any disclaimer, the term of this patent is extended or adjusted under 35 U.S.C. 154(b) by 1436 days.

(21) Appl. No.: 11/082,180

(22) Filed: Mar. 16, 2005

(65) Prior Publication Data
US 2006/0210494 A1 Sep. 21, 2006

(51) Int. Cl.
*A61F 2/00* (2006.01)
*A61K 9/16* (2006.01)

(52) U.S. Cl.
USPC .......................................... 424/489; 424/423

(58) Field of Classification Search
USPC ................................. 424/489, 423
See application file for complete search history.

(56) References Cited

U.S. PATENT DOCUMENTS 6,730,324 B2 * 5/2004 Troczynski et al. ........... 424/489
2004/0033249 A1 * 2/2004 Sewing et al. ................ 424/423

OTHER PUBLICATIONS

Nakano et al., Control of hydroxyapatite crystallinity by mechanical grinding method, J. of Mater. Sci.: Materials in Medicine, 2001, pp. 703-706.*
Sun, L. et al., Surface characteristics and dissolution behavior of plasm-sprayed hydroxyapatite coating, J. Biomed. Mater. Res., 2002, 62, pp. 228-236.*
Choi et al., Ion-beam-assisted-deposition (IBAD) of hydroxyapatite coating layer on Ti-based metal substrate, Biomaterials, 2000, 21, pp. 469-473.*
Huang et al., Ion beam assisted deposition of TiN thin film on Si (100), Mater. Chem. and Physics, 1999,59, pp. 49-56.*
Low, I., Depth-profiling of crystal structure, texture, and microhardness in a functionally graded tooth enamel, J. Am. Ceram. Soc., 2004, 87(11), pp. 2125-2131.*
Verde-Carvallo et al., Mineralization of Hydroxyapatite over Collagen Type I, European Cells and Materials, 2002, 7, supplement 2, pp. 58-59.*
Shirkhanzedeh, M., Direct formation of nanophase hydroxyapatite on cathodically polarized electrodes, Journal of Materials Science: Materials in Medicine, 1998, 9, pp. 67-72.*
Webster et al., Hydroxyapatite with substituted magnesium, zinc, cadmium, and yttrium. II. Mechanisms of osteoblast adhesion, Journal of Biomaterials Research, 2002, 9, pp. 312-317.*
Wang et al., Development of bimimetic nano-hydroxyapatite/poly(hexamethylene adipamide) composites, Biomaterials, 2002, 23, pp. 4787-4791.*
Bloebaum, R.D., et al., "Retrieval Analysis of a Hydroxyapatite-Coated Hip Prosthesis," *Clin. Orthop. Rel. Res.*, 1991, pp. 97-102, vol. 267.

(Continued)

*Primary Examiner* — Benjamin Packard
(74) *Attorney, Agent, or Firm* — Womble, Carlyle Sandridge & Rice, LLP

(57) ABSTRACT

The present invention provides a biocompatible coating comprising calcium phosphate that is functionally graded across the thickness of the coating. The coating, which preferably includes hydroxyapatite, is particularly useful for coating implants, such as dental or orthopedic implants. The functionally graded coating is generally crystalline near the interface with the surface of the implant, with crystallinity and crystal diameter decreasing toward the outer layer of the coating. The invention further provides methods for preparing a coated implant comprising a functionally graded calcium phosphate coating thereon.

20 Claims, 6 Drawing Sheets

OTHER PUBLICATIONS

Cao, Y., et al., "Water Vapour-Treated Hydroxyapatite Coatings after Plasma Spraying and Their Characteristics," *Biomaterials*, 1996, pp. 419-424, vol. 17(4).

Chou, L., et al., "Effects of Hydroxylapatite Coating Crystallinity on Biosolubility, Cell Attachment Efficiency and Proliferation In Vitro," *Biomaterials*, 1999, pp. 977-985, vol. 20.

Cooley, D.R., et al., "The Advantages of Coated Titanium Implants Prepared by Radiofrequency Sputtering from Hydroxyapatite,"*J Prosthet. Dent.*, 1992, pp. 93-100, vol. 67.

Cook, S.D., et al., "The Effect of Surface Macrotexture on the Mechanical and Histologic Characteristics of Hydroxylapatite-Coated Dental Implants," *J Oral Implant*, 1993, pp. 288-294, vol. 19(4).

Dalton, J.E. and Cook, S.D., "In Vivo Mechanical and Histological Characteristics of HA-Coated Implants Vary with Coating Vendor,"*J Biomed Mater Res.*, 1995, pp. 239-245, vol. 29.

De Bruijn, J.D., et al., "Influence of Crystal Structure on the Establishment of the Bone-Calcium Phosphate Interface In Vitro," *Cells and Mater*, 1993, pp. 407-417, vol. 3(4).

Ding, S., et al., "Characterization of Hydroxyapatite and Titanium Coatings Sputtered on Ti-6A1-4V Substrate," *J. Biomedical Mater. Res.*, 1999, pp. 266-279, vol. 44.

Feddes, B., et al., "Bulk Composition of R.F. Magnetron Sputter Deposited Calcium Phosphate Coatings on Different Substrates (Polyethylene, Polytetrafluoroethylene, Silicon)," *Surf. Coat. Technol.*, 2004, pp. 346-355, vol. 185.

Filiaggi, M.J., et al., "Characterization of the Interface in the Plasma-Sprayed HA Coating/Ti-6A1-4V Implant System,"*J. Biomed. Mater. Res.*, 1991, pp. 1211-1229, vol. 25.

Gabbi, C., et al., "Physical, Chemical and Biological Characterisation of Hydroxyapatite Coatings of Differentiated Crystallinity," *Fourth World Biomaterials Congress*, Berlin, Germany, Apr. 24-28, 1992, p. 5.

Hench, L. L., and Ratner, B. D. (Ed.), "Ceramics, Glasses, and Glass-Ceramics," *Biomaterials Science: An Introduction to Materials in Medicine*, 1996, p. 73-84, Academic Press, San Diego.

Kay, J.F., "Calcium Phosphate Coatings for Dental Implants—Current Status and Future Potential," *Dent. Clin. North Amer.*, 1992, pp. 1-18, vol. 36(1).

Kumar, R. R. And Wang, M., "Modulus and Hardness Evaluations of Sintered Bioceramic Powders and Functionally Graded Bioactive Composites by Nano-Indentation Technique," *Materials Science and Engineering*, 2002, pp. 230-236, vol. A338.

Lacefield, W.R., "Characterization of Hydroxylapatite Coatings," *J Oral Implant*, 1994, pp. 214-220, vol. 20(3).

Lacefield, W.R. in Ducheyne, P. and Lemons, J.E. ed., "Hydroxyapatite Coatings," *Bioceramics: Material Characteristics Versus In Vivo Behavior*, 1998, pp. 72-80, The New York Academy of Science, New York.

Van Dijk, K., et al., "Influence of Annealing Temperature on RF Magnetron Sputtered Calcium Phosphate Coatings," *Biomaterials*, 1996, pp. 405-410, vol. 17(4).

Yan, L., et al., "Characterization of Chemical Inhomogeneity in Plasma-Sprayed Hydroxyapatite Coatings," *Biomaterials*, 2003, pp. 2585-2592, vol. 24.

Yang, Y., et al., "A Review on Calcium Phosphate Coatings Produced Using a Sputtering Process—An Alternative to Plasma Spraying," *Biomaterials*, 2005, pp. 327-337, vol. 26.

Zablotsky, M.H., "The Surgical Management of Osseous Defects Associated with Endosteal Hydroxyapatite-Coated and Titanium Dental Implants," *Dent. Chn. North. Amer.*, 1992, pp. 117-149, vol. 36(1).

Guise, T., et al., "Interleukin-1 Receptor Antagonist Inhibits the Hypercalcemia Mediated by Interleukin-1," *J. Bone Miner. Res.*, 1993, pp. 583-587, vol. 8(5).

Hoppe, C., et al., "Osteoblast Response to HA Ceramics of Different Crystallinity," *J. Dent. Res.*, 1996, p. 78, vol. 75, Abstract No. 482.

Legeros, R. in Meyers, H., ed., "Calcium Phosphate Biomaterials in Preventive and Restorative Dentistry," *Monographs in Oral Science*, 1991, pp. 154-192, Karger, Basel, Switzerland.

Passi-Even, L., et al., "Ontogenesis of Ultrastructural Features During Osteogenic Differentiation in Diffusion Chamber Cultures of Marrow Cells," *J. Bone Miner. Res.*, 1993, pp. 589-595, vol. 8(5).

Radin, S., et al., "Plasma Spraying Induced Changes of Calcium Phosphate Ceramic Characteristics and the Effect on In Vitro Stability," *J. Mater. Sci. Mater. Med.*, 1992, pp. 33-42, vol. 3.

Schneider, G., et al., "Implant Surface Roughness Affects Osteoblast Gene Expression," *J. Dent. Res.*, 2003, pp. 372-376, vol. 82(5).

Kaufman, H.R., et al., "Target Processes," *Operation of Broad-Beam Sources*, 1987, pp. 107-117, Commonwealth Scientific Corporation, Alexandria, VA.

Legeros, R., "Calcium Phosphate Materials in Restorative Dentistry: A Review," *Adv in Dent Mater*, 1988, pp. 164-180, vol. 2(1).

Lemons, J., "Hydroxyapatite Coatings," *Clin. Orthop.*, 1988, pp. 220-223, vol. 235.

Lewis, G., "Hydroxyapatite-Coated Bioalloy Surfaces: Current Status and Future Challenges," *Biomed. Mater. Eng.*, 2000, pp. 157-188, vol. 10.

Lucas, L. C., et al., "Calcium Phosphate Coatings for Medical and Dental Implants," *Colloids and Surfaces A: Physiochemical and Engineering Aspects*, 1993, pp. 141-147, vol. 77.

Luo, Z. S., et al., "Low-Temperature Crystallization of Calcium Phosphate Coatings Synthesized by Ion-Beam-Assisted Deposition," *J. Biomed. Mater. Res.*, 1996, pp. 80-86, vol. 46.

Martin, R.B., "Biomaterials," *Introduction to Bioengineering*, 1996, pp. 339-360, Oxford University Press, Oxford, UK.

Nery, E.B., et al., "Tissue Response to Biphasic Calcium Phosphate Ceramic with Different Ratios of HA/βTCP in Periodontal Osseous Defects," *J. Periodontal*, 1992, pp. 729-735, vol. 63(9).

Ozeki, K., et al., "Phase Composition of Sputtered Films from a Hydroxyapatite Target," *Surf. Coat. Technol.*, 2002, pp. 54-61, vol. 160.

Rabiei, et al., "Processing and Development of Nano-Scale HA Coatings for Biomedical Application," *Journal of Mater. Sci. And Eng.*, vol. C, in review, 2005.

Rivero, D.P., et al., "Calcium Phosphate-Coated Porous Titanium Implants for Enhanced Skeletal Fixation," *J Biomed. Mater. Res.*, 1988, pp. 191-201, vol. 22.

Silva, P., et al., "Adhesion and Microstructural Characterization of Plasma-Sprayed Hydroxyapatite/Glass Ceramic Coatings onto Ti-6A1-4V Substrates," *Surf. Coat. Technol.*, 1998, pp. 191-196, vol. 102.

Søballe, K., et al., "Hydroxyapatite Coating Converts Fibrous Tissue to Bone around Loaded Implants," *J Bone Joint Surg*, 1993, pp. 270-277, vol. 75-B(2).

Thomas, K.A. and Cook, S.D., "An Evaluation of Variables Influencing Implant Fixation by Direct Bone Apposition," *J. Biomed. Mater. Res.*, 1985, pp. 875-901, vol. 19.

\* cited by examiner

FUNCTIONALLY GRADED BIOCOMPATIBLE COATING AND COATED IMPLANT

FIELD OF THE INVENTION

The present invention relates to biocompatible coatings. In particular, the invention is related to implants coated with a biocompatible calcium phosphate coating and methods of preparation of such coated implants.

BACKGROUND OF THE INVENTION

Various types of implants are commonly used in biomedical applications, particularly in the dental and orthopedic fields. Often, implants are associated with use in areas of hard tissue (i.e., cartilage, bone, etc.), and the implants generally comprise hard, durable materials, such as metals, particularly titanium.

Uncoated titanium implants are normally covered by a bioinert surface of titanium dioxide. The presence of the bioinert surface structure prohibits biointegration of the implant by the surrounding tissue. Accordingly, the body responds to the foreign object by isolating the implant with a flexible layer of fibrous tissue that can easily cause an implant to loosen. This is detrimental to the usefulness of the implant. For example, in the case of dental implants, loosening of the implant can result in loss of the implanted tooth and can also lead to infections around the loosened implant.

It is commonly known in the art to apply various coatings to orthopedic components and other medical devices for a variety of reasons, including facilitating implant fixation and bone in-growth. See, *Handbook of Materials for Medical Devices*, Davis, J. R. (Ed.), Chapter 9, "Coatings", (2003). In particular, calcium phosphate phases are useful as coatings for facilitating bone in-growth. One calcium phosphate phase, hydroxyapatite (HA) $[Ca_{10}(PO_4)_6(OH)_2]$, is the primary mineral content of bone and calcified cartilage, representing 43% by weight of bone. Because of the chemical and crystallographic similarities with the inorganic components of bone, applying a thin layer of HA, or other calcium phosphate layer, to the surface of a metal implant, such as a titanium implant, can promote osseointegration and increase the mechanical stability of the implant. In fact, many studies have demonstrated that dental and orthopedic implants coated with plasma sprayed HA promote greater direct bone attachment and higher interfacial strength compared to the uncoated titanium implants. Numerous problems with the HA coatings, however, have also been cited, including variation in bond strength at the coating-metal interface, variation in structural and chemical properties, and non-uniformity in coating density.

Hydroxyapatite coatings are generally comprised of varying percentages of crystalline HA, tricalcium phosphate, and amorphous calcium phosphate. The ratio of HA to tricalcium phosphate has been reported to be crucial for bone regeneration. It has also been reported that the dissolution rate of a HA coating is correlated to the biochemical calcium phosphate phase of the coating. It is known that coatings with more crystalline HA are more resistant to dissolution. Conversely, coatings with increased concentrations of amorphous calcium phosphate and tricalcium phosphate are thought to predispose the HA coatings to dissolution. Since it has been suggested that the dissolution of calcium phosphate from the surface of the implant in the body is responsible for the bioactivity of the HA coating, knowledge of the crystalline content of the surface coating is critical to implant success. Some studies have indicated that bone responds differently to HA coatings of different crystallinity. These studies have indicated higher bone activity with well characterized HA coatings of higher crystallinity, while other studies suggest that some amorphous phase in the coatings is desirable and promotes a more stable interface with the biological environment. Still further studies have identified various structural factors that also affect the biological response of bone to HA coatings, including surface texture, porosity, and the presence of trace elements. Accordingly, it is beneficial for the characteristics of the implant surface to be precisely controlled during the implant process, particularly with respect to the crystalline content of the coating surface.

Traditional HA coatings are deposited by various techniques, such as sputtering, electron beam deposition, laser deposition, and plasma spraying. Because of its simplicity and versatility, plasma spraying is the most widely used technique. Although plasma spraying is fast and cost effective, the coatings have several flaws that could lead to implant failures. Plasma sprayed films exhibit a high porosity and only attach to the substrate surface through mechanical bonding (i.e., no intermolecular bonding). This leads to inconsistent bonding strengths. Further, regardless of the coating methodology, amorphous layers are generally formed on metal substrates, which have a high dissolution rate in aqueous solutions. Therefore, the layers are often subsequently heat-treated at approximately 600° C. to convert the amorphous phase into a crystalline phase. This heat treatment, however, causes cracks in the layer due to the thermal expansion mismatch between the coated layer and the metal substrate. This leads to a severe reduction in bond strength.

Plasma sprayed coatings are also relatively thick. Generally, coatings on commercially available plasma sprayed implants have a thickness of between 79 μm and 111 μm. Such thick coatings can lead to low fracture resistance. This, along with reduced bond strength, can lead to delamination, and detached fragments have very adverse effects on the implant, as well as the tissue surrounding it. For example, particulate debris at the bone prostheses interface with HA coated implants has been found to cause a foreign body response that is destructive to the surrounding tissues. As a result, improvement of the HA coating properties may reduce shedding and possibly prevent an aggressive osteolytic response. Some studies have indicated that thin HA coatings (about 2 μm) have a significantly greater coating-metal interfacial strength compared to commercially available thick (70 μm) plasma sprayed HA coatings (40 MPa versus 9 MPa, respectively).

SUMMARY OF THE INVENTION

According to one aspect of the invention, there is provided a biocompatible coating comprising a calcium phosphate film having a plurality of layers. In one particular embodiment, the film comprises a bottom layer, one or more intermediate layers, and a top layer. The calcium phosphate film is functionally graded in at least one of crystallinity and crystal size (particularly crystal diameter). In one particular embodiment, the calcium phosphate film is functionally graded in crystallinity and crystal size such that degree of crystallinity and crystal size both decrease from the bottom layer to the top layer.

In one embodiment of the invention, the calcium phosphate is selected from the group consisting of hydroxyapatite, tricalcium phosphate, and mixtures thereof. Preferably, the film is functionally graded such that the bottom layer comprises predominately crystalline calcium phosphate with crystals in a given crystal size range, the one or more intermediate layers comprise crystalline calcium phosphate with crystals of a smaller size than in the bottom layer, and the top layer comprises a mixture of crystalline calcium phosphate (the crystals being generally smaller than in the one or more intermediate layers) and amorphous calcium phosphate. Most preferably, the top layer is predominately amorphous calcium phosphate.

According to another aspect of the invention, there is provided a biocompatible coated substrate comprising a substrate having a surface and a biocompatible coating on the surface of the substrate. In one embodiment, the biocompatible coating comprises a calcium phosphate film having an inner layer bonded to the surface of the substrate, one or more intermediate layers, and an outer layer. Preferably, the film is functionally graded in at least one of crystallinity and crystal diameter such that crystallinity and crystal diameter decrease from the inner layer to the outer layer.

In one particular embodiment, the invention provides a coated dental implant comprising a dentally implantable substrate having a surface that is at least partially coated with a calcium phosphate film having an inner layer bonded to the surface of the substrate, one or more intermediate layers, and an outer layer, wherein the film is functionally graded in crystallinity and crystal diameter such that crystallinity and crystal diameter both gradually decrease from the inner layer to the outer layer. According to another particular embodiment, the invention provides a coated orthopedic implant comprising an orthopedically implantable substrate having a surface that is at least partially coated with a calcium phosphate film having an inner layer bonded to the surface of the substrate, one or more intermediate layers, and an outer layer, wherein the film is functionally graded in crystallinity and crystal diameter such that crystallinity and crystal diameter both gradually decrease from the inner layer to the outer layer.

According to another aspect of the invention, there is provided a method for preparing a biocompatible coated substrate. In one embodiment, the method comprises providing a substrate having a surface, heating the substrate to a beginning deposition temperature, applying a calcium phosphate film to the surface of the substrate, and manipulating the deposition temperature during the applying step. The method is effective for forming a coating on the substrate comprising a calcium phosphate film having an inner layer bonded to the surface of the substrate, one or more intermediate layers, and an outer layer, wherein the film is functionally graded in at least one of crystallinity and crystal size such that crystallinity and crystal size decrease from the inner layer to the outer layer.

In one particular embodiment, the film is functionally graded such that the degree of crystallinity decreases from the inner layer to the outer layer. In still another embodiment, the film is functionally graded such that degree of crystallinity and the crystal size both decrease from the inner layer to the outer layer.

BRIEF DESCRIPTION OF THE DRAWINGS

The present invention is more fully illustrated by the following examples, which are set forth to illustrate the present invention and are not to be construed as limiting.

DETAILED DESCRIPTION

Figure 1:
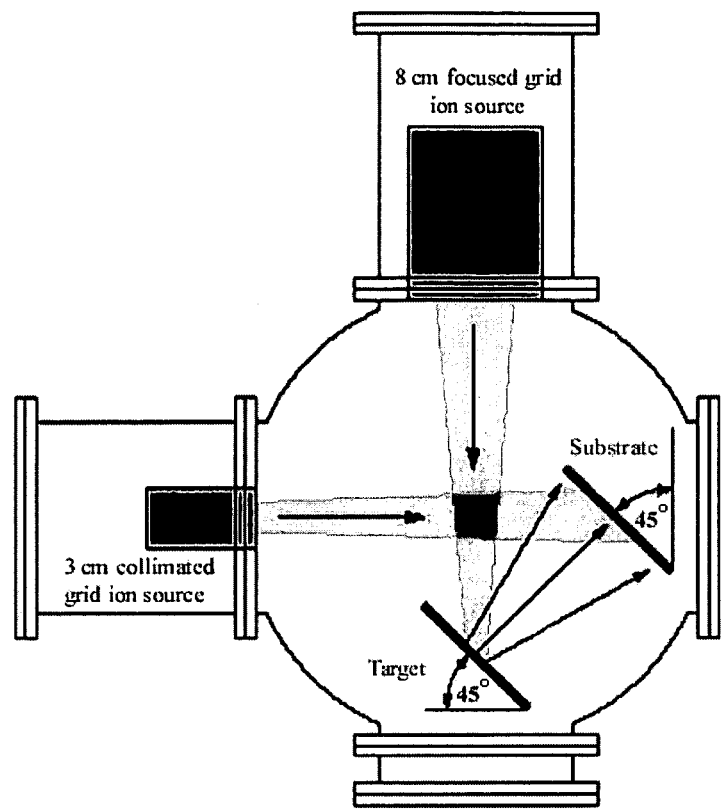
FIG. 1 is one embodiment of a dual ion beam sputtering system useful for depositing a coating according to the invention on a substrate.

The invention now will be described more fully hereinafter with reference to the accompanying drawings, in which preferred embodiments of the invention are shown. These embodiments are provided so that this disclosure will be thorough and complete, and will fully convey the scope of the invention to those skilled in the art.

The present invention provides a functionally graded coating, coated substrates coated with the functionally graded coating, and methods of preparing such coated substrates. The coating is characterized by a gradual decrease in at least one of the crystallinity and the crystal grain size (particularly the crystal diameter) across the thickness of the coating. The bottom (or inner) portion of the coating generally comprises crystalline phase material of relatively large crystal size (compared to the remaining portions of the coating). The crystallinity and crystal size gradually decrease moving toward the top (or outer) portion of the coating leading to crystal grains of smaller and smaller size and a reduction in the extent of crystallinity, eventually becoming predominately amorphous at the top (or outer) surface of the coating.

The coatings of the invention are described in terms of being functionally graded across the thickness of the coating. Functionally graded materials are understood to comprise materials wherein the composition, the microstructure, or both are locally varied so that a certain variation of the local material properties is achieved. Functionally graded coatings are particularly useful in that they can be structurally engineered to allow for discrete or continual variations in the molecular modeling of the coating. This allows for preparation of coatings with varying thermal, mechanical, and even bioactive properties across the thickness of the coating. The present invention allows for an even greater ability to engineer the coating on an atomic level to nanostructure the coating to predetermined specifications that maximize strength and durability in one phase of the coating while maximizing bioavailability (e.g., osseointegration) in another phase of the coating.

According to the present invention, functionally graded calcium phosphate coatings are provided. The coatings are functionally graded in that at least one of degree of crystallinity and crystal grain size changes according to predetermined parameters across the thickness of the coating. Preferably, the coatings are functionally graded such that at least one of degree of crystallinity and crystal grain size decreases from the bottom layer of the coating to the top layer of the coating. In one particular embodiment of the invention, the coating is functionally graded in degree of crystallinity from the bottom layer to the top layer such that the calcium phosphate is predominately crystalline in the bottom layer and crystallinity decreases moving toward the top layer such that the calcium phosphate is predominately amorphous in the top layer. Degree of crystallinity, as used herein, refers to the relative percentage of the calcium phosphate material present that is in a crystalline phase versus that present in a non-crystalline phase (e.g., an amorphous phase). A high degree of crystallinity would indicate the material present is predominately in a crystalline phase. A low degree of crystallinity would indicate the material present predominately in a non-crystalline phase.

In another embodiment of the invention, the coating is functionally graded such that both degree of crystallinity and crystal grain size changes according to predetermined parameters across the thickness of the coating. Preferably, degree of crystallinity and crystal grain both decrease from the bottom layer of the coating to the top layer of the coating. In one particular embodiment, the coating comprises a bottom layer, one or more intermediate layers, and a top layer. In this embodiment, the bottom layer has a high degree of crystallinity and crystal grain size of large size in relation to the remaining layers of the coating. In the one or more intermediate layers of this embodiment, the degree of crystallinity is less than or equal to the degree of crystallinity in the bottom layer, and the crystal grain size of the crystalline material is less than the crystal grain size in the bottom layer. In the top layer of this embodiment, the degree of crystallinity is less than the intermediate layer and the bottom layer. Preferably, the degree of crystallinity in the top layer is low, more preferably the material is predominately amorphous. Further, in this embodiment, the crystal grain size of any crystals present in the top layer is smaller than the crystal grain size in the intermediate layer or the bottom layer.

Description in terms of crystal grain size can vary depending upon the type of material present and the crystalline shape inherent to the material. In the present invention, calcium phosphate can be present in various different embodiments. In one embodiment, the calcium phosphate is present as tricalcium phosphate ($Ca_3(PO4)_2$). In another embodiment, the calcium phosphate is present as hydroxyapatite. In yet another embodiment, both tricalcium phosphate and hydroxyapatite are present. Preferably, at least a portion of the calcium phosphate is in the form of hydroxyapatite. In one particular embodiment, the calcium phosphate comprises predominantly hydroxyapatite. For purposes of simplicity, the coatings of the invention may be described throughout in relation to an embodiment of the invention wherein the calcium phosphate is hydroxyapatite. Description of the coating in terms of comprising hydroxyapatite, however, should not be interpreted as limiting the coatings to that single embodiment. Rather, the coatings can comprise other calcium phosphate materials, as previously noted.

Both tricalcium phosphate and hydroxyapatite, when in crystalline thin film sputter deposited form, are generally columnar shaped crystals. Accordingly, crystal grain size for such columnar shaped crystals can be described both in terms of crystal length and crystal diameter. As used herein, crystal grain size is generally understood to relate to crystal diameter. Accordingly, the terms crystal grain size and crystal diameter can be used interchangeably.

Preferably, the coatings of the invention are functionally graded such that crystallinity and crystal grain size decrease moving in the same direction across the thickness of the coating. Accordingly, the coating can be characterized as comprising a bottom layer, a top layer, and one or more intermediate layers. When the coating is applied to a substrate, the bottom layer is referred to as the inner layer as it is the layer interfacing with the substrate surface. Further, when applied to a substrate, the top coating layer is referred to as the outer layer.

The various layers comprising the coating can have well-defined boundaries. Alternately, the various layers can transition more gradually from one to another. Further, such transitioning can be so gradual such that the description in terms of "layers" is more of an abstract characterization of the coating used solely to describe the functionally graded state of the coating and is less of an actual visual description of the coating. Such transitioning can be strongly affected by the method of preparation of the coating, which is described in greater detail below. Further, it is possible for a single coating to have portions where the transition is gradual and also have portions where the layer boundaries are well-defined.

In one aspect of the invention, the biocompatible coating comprising a calcium phosphate film having a bottom layer, one or more intermediate layers, and a top layer. The film is functionally graded in crystallinity and crystal diameter such that crystallinity and crystal diameter both decrease from the bottom layer to the top layer.

In one particular embodiment of the invention, the bottom layer of the coating comprises predominately crystalline calcium phosphate. Preferably, the crystalline calcium phosphate in the bottom layer comprises crystals having a diameter of about 2 nm to about 50 nm. More preferably, the bottom layer comprises crystals having a diameter of about 5 nm to about 30 nm, most preferably about 5 nm to about 20 nm. Generally, the bottom layer can include crystals of diameter sizes varying throughout the ranges noted above intermixed throughout the layer. The crystals in the bottom layer preferably have a size distribution such that more crystals are of a size toward the upper end of the size range than toward the lower end of the size range.

The coating also can be functionally graded within an individual layer. For example in the bottom layer, the crystalline calcium phosphate near the bottom portion of the bottom layer can generally comprise crystals of greater diameter than the crystals near the upper portion of the bottom layer. Additionally, an individual layer can be functionally graded in terms of degree of crystallinity. In the bottom layer, while it is preferred that the layer comprise predominately crystalline calcium phosphate, the layer can, to some degree, also comprise amorphous calcium phosphate. Accordingly, the bottom layer can be functionally graded within the layer such that the calcium phosphate near the bottom portion of the bottom layer is at or about 100% crystalline, while the calcium phosphate near the top portion of the bottom layer includes a higher percentage of amorphous calcium phosphate. Such functional grading within a specific layer can also be present in the remaining layers of the coating of the invention, particularly in the one or more intermediate layers.

The thickness of the bottom layer can vary depending upon the intended use of the coating, the method of formation of the coating, and the substrate to which the coating may be applied. In one embodiment, the bottom layer of crystalline calcium phosphate has a thickness that comprises up to about 50% of the overall thickness of the coating. In another embodiment, the bottom layer has a thickness of about 50 nm to about 1,000 nm.

The one or more intermediate layers particularly provide a transition area for the calcium phosphate coating. The one or more intermediate layers can consist of a single layer that is, preferentially, functionally graded throughout. In other embodiments, two or more intermediate layers can be present, each individual intermediate layer having a discrete composition (i.e., degree of crystallinity and range of crystal diameter), or each individual layer being functionally graded throughout. As used throughout, the intermediate layer may be described in terms of a single layer. However, it is understood that the invention encompasses the presence of one or more intermediate layers, each possibly taking on the description provided herein.

While the bottom layer can include crystalline and amorphous calcium phosphate, it is preferable for the bottom layer to be predominately crystalline calcium phosphate (i.e., close to 100%). In the intermediate layer, however, there can be greater variations in the degree of crystallinity. Preferably, the portion of the intermediate layer near the bottom layer has a greater percentage of crystalline calcium phosphate and a lesser percentage of amorphous calcium phosphate. Further, preferably, the percentage of amorphous calcium phosphate in the intermediate layer increases (and the percentage of crystalline calcium phosphate decreases) through the intermediate layer moving away from the bottom layer. However, in further embodiments, the intermediate layer has a composition wherein the degree of crystallinity is substantially uniform throughout the layer. In such embodiments, it is preferable for the intermediate layer to have a greater percentage of amorphous calcium phosphate than the bottom layer but have a lesser percentage of amorphous calcium phosphate than the top layer.

Similarly, the crystal diameter of the crystalline calcium phosphate throughout the intermediate layer is preferably generally smaller than the crystal diameter of the crystalline calcium phosphate in the bottom layer. Again, the crystal diameter can be substantially uniform throughout the intermediate layer, or the intermediate layer can be functionally graded such that the crystal diameter of the crystalline calcium phosphate decreases throughout the intermediate layer moving away from the bottom layer. When the crystal diameter is substantially uniform, it is preferable for the crystal diameter generally to be less than the crystal diameter of the crystalline calcium phosphate in the bottom layer. When two or more intermediate layers are present, the crystal diameter of the crystalline calcium phosphate can be functionally graded across each of the intermediate layers, preferably such that the crystal diameter of the crystalline calcium phosphate is generally smaller in each succeeding intermediate layer moving away from the bottom layer.

Also similar to the bottom layer, the crystal diameter of the crystalline calcium phosphate in the intermediate layer can vary across a range of diameter sizes. Preferably, a greater percentage of the crystalline calcium phosphate in the intermediate layer has a crystal diameter in the lower range of the crystal diameter size. In one embodiment, the crystal diameter of the crystalline calcium phosphate in the intermediate layer is about 2 nm to about 20 nm. Preferably, the crystal diameter is about 2 nm to about 15 nm, more preferably about 2 nm to about 10 nm. While there can be some overlap in crystal diameter between the bottom layer and the intermediate layer, the crystal diameter of the calcium phosphate in the intermediate layer is generally smaller than the crystal diameter of the calcium phosphate in the bottom layer.

As with the bottom layer, the thickness of the intermediate layer can vary depending upon the intended use of the coating, the method of formation of the coating, and the substrate to which the coating may be applied. Further, the thickness of the intermediate layer can vary depending upon the number of intermediate layers present, which can affect how gradually, or how quickly, the coating is graded across the thickness of the coating. In one embodiment, the intermediate layer of crystalline calcium phosphate has a thickness that comprises up to about 50% of the overall thickness of the coating. In another embodiment, the intermediate layer has a thickness of about 50 μm to about 1,000 nm.

As the coating is functionally graded across the thickness of the coating, it can generally be characterized as transitioning from one structural state near the bottom of the coating to another structural state near the top of the coating. As described above, the coating is preferably predominately crystalline calcium phosphate with relatively large crystal diameter near the bottom of the coating. Accordingly, the coating is preferably predominately amorphous calcium phosphate near the top of the coating.

The top layer of the coating, as with the previous layers, can have a composition that is substantially uniform throughout the layer in relation to the degree of crystallinity and the crystal diameter of the crystalline calcium phosphate present in the top layer. Alternately, the top layer can be functionally graded across the thickness of the layer, the percent of amorphous calcium phosphate being lesser near the bottom portion of the top layer and being greater near the top portion of the top layer. Preferably, the calcium phosphate in the top layer is predominately amorphous calcium phosphate. In one embodiment, at least about 50% of the calcium phosphate in the top layer is amorphous calcium phosphate. Preferably, at least about 75% of the calcium phosphate in the top layer is amorphous calcium phosphate, more preferably at least about 90% of the calcium phosphate in the top layer is amorphous calcium phosphate. In one embodiment, the top layer of the coating consists essentially of amorphous phase calcium phosphate.

While is preferable for the calcium phosphate in the top layer to be predominately amorphous calcium phosphate, it is possible for at least a portion of the calcium phosphate in the top layer to be crystalline calcium phosphate. Accordingly, it is also preferred for the crystalline calcium phosphate in the top layer of the coating to have a crystal diameter generally that is less than the crystal diameter generally found in the intermediate layer or in the bottom layer. Again, while there can be an overlap in the ranges of crystal diameter sizes across the various layers, preferentially, the crystal diameter in the top layer is generally less than in the remaining layers. In one embodiment, the crystal diameter of the crystalline calcium phosphate in the top layer is less than about 15 nm. Preferably, the crystal diameter of the crystalline calcium phosphate in the top layer is less than about 10 nm, more preferably less than about 5 nm, and even more preferably, less than or equal to about 2 nm.

As before, the thickness of the top layer can vary depending upon the intended use of the coating, the method of formation of the coating, and the substrate to which the coating may be applied. In one embodiment, the top layer of crystalline calcium phosphate has a thickness that comprises up to about 50% of the overall thickness of the coating. In another embodiment, the bottom layer has a thickness of about 50 nm to about 1,000 nm.

In addition to calcium phosphate, it is possible for the coating of the invention to include one or more additional components useful for increasing the biocompatibility, including osseointegration, of the coating. In one embodiment, the coating can comprise at least one further component commonly found in physiological bone that exhibits a high affinity between the ion of the component with calcium in serum. Examples of such further components include, but are not limited to zinc, magnesium, and fluoride. Still further, the coating can include other components not commonly found in physiological bone so long as the component exhibits a high affinity to calcium in serum. Such components are generally known to increase the stability and mechanical properties of the hydroxyapatite, as well as increasing the initial calcium absorption of the HA coating from serum. Initial calcium absorption has been shown to be critical for promoting new bone synthesis as it leads to the binding of specific proteins that selectively enhance bone cell formation in and around the coating, enhancement bone cell attachment to the coating, and facilitation of proper function of the coating in bone integration. In one particular embodiment of the invention, the calcium phosphate coating further comprises an amount of yttrium.

Preferably, at least one further component is present only as a relatively small percentage of the calcium phosphate coating (i.e., a doping amount). In one embodiment, the calcium phosphate coating comprises up to about 10%, on a molar basis, of yttrium. Preferably, the coating comprises up to about 8%, on a molar basis, of yttrium, more preferably about 6%, on a molar basis.

The calcium phosphate coating of the invention is particularly useful as a coating for a substrate, such as an implant. Accordingly, the present invention further provides coated substrates comprising a substrate having a surface and a biocompatible coating covering at least a portion of the surface of the substrate. The coating comprises a calcium phosphate film having an inner layer bonded to the surface of the substrate, one or more intermediate layers, and an outer layer. The film is functionally graded in at least one of crystallinity and crystal diameter such that crystallinity and crystal diameter changes from the inner layer of the coating to the outer layer of the coating. Preferably, at least one of crystallinity and crystal diameter decreases from the inner layer of the coating to the outer layer of the coating. In one particular embodiment, both crystallinity and crystal diameter decrease from the inner layer of the coating to the outer layer of the coating.

The substrate according to the invention can include any item or device wherein the presence of a biocompatible coating, particularly a coating providing increased osseointegration, would be advantageous. Preferably, the substrate is an item or device implantable in an area where interaction or integration with bony formations is desired or expected. In one embodiment of the invention, the substrate includes a prosthetic implant. According to another embodiment, the substrate includes a dental implant. In yet another embodiment of the invention, the substrate includes an orthopedic implant. Items useful as substrates for coating according to the invention include, but are not limited to the following: dental screws, cylinders, blades, plates, and posts; partial or total joint replacements, including hip, knee, shoulder, and ankle replacements; orthopedic screws, pins, plates, bolts, nuts, rods, nails, and wires; and other similar dentally or orthopedically implantable substrates.

The substrate coated according to the invention can comprise any material generally recognized by one of skill in the art as being useful as an implantable item or device. In particular, the substrate can comprise a material generally recognized as being useful as an implant in or around bony formations. In one embodiment of the invention, the substrate comprises one or more metallic material. Particularly, the substrate comprises a material selected from the group consisting of titanium, titanium alloys, cobalt/chromium alloys, steel, and mixtures thereof. The invention, however, is not limited to these particular embodiments; rather, the substrate can include various additional materials that may provide additional desirable properties or functionality to the substrate.

The coated substrate of the invention is particularly useful in the dental orthopedic fields. Accordingly, in one embodiment of the invention, the substrate comprises a titanium dental implant. In another embodiment, the substrate comprises a titanium orthopedic implant.

Coates substrates according to the invention are also useful generally in the area of bone reconstruction. For example, the coated substrate could be used in a partial or total joint replacement, in replacement of an area of missing bone, and as a piece for treating bone fracture, such as a screw or plate.

The coated substrate of the invention derives particular advantages from the functionally graded coating applied to the substrate. In this embodiment of the invention, the coating can be characterized as comprising an inner coating layer interfacing with surface of the substrate, one or more intermediate layers, and an outer layer overlying the one or more intermediate layers.

The inner layer of the functionally graded coating comprises predominately crystalline calcium phosphate of relatively large crystal diameter, particularly at the interface of the inner layer with the surface of the substrate. Maximizing crystallinity at the interface with the substrate increases the strength and the lifetime of the coating on the substrate.

In one embodiment of the invention, the crystallinity and crystal diameter of the calcium phosphate coating gradually decreases moving away from the surface of the substrate and toward to the outer surface of the coating. The transition from higher crystallinity and greater crystal diameter to lesser crystallinity and smaller crystal diameter is particularly seen moving from the inner layer, across the intermediate layer, and into the outer layer. Accordingly, the intermediate layer comprises a mixture of crystalline and amorphous calcium phosphate, as well as crystals with a diameter spanning a range of sizes. The outer layer of the coating is predominately amorphous calcium phosphate, and any crystalline calcium phosphate is of a relatively small crystal diameter.

Maximizing the amorphous nature of the calcium phosphate in the outer layer of the coating increases the biocompatibility of the coating, particularly by facilitating faster calcium absorption. The amorphous calcium phosphate exhibits greater biodegradability than crystalline calcium phosphate. Accordingly, the amorphous calcium phosphate in the outer layer of the coating facilitates the creation of channels and pores in the coating through which osseointegration can take place. Accordingly, the ability of surrounding bone to directly bond with the coated substrate is increased by the presence of the coating, particularly due to the presence of the outer, amorphous layer. Complete biodegradability of the coating, however, does not take place due to the presence of the inner, highly crystalline layer, which stabilizes the coating on the substrate. In this manner, the functionally graded coating facilitates integration and stabilization of the implant at the desired site of implantation. Furthermore, the coating limits competitive cell function at the implantation site.

The description of the calcium phosphate coating previously provided is also applicable to the calcium phosphate film of the biocompatible coating used on the coated substrate of the invention. Therefore, it is understood that the calcium phosphate film on the coated substrates of the invention includes each of the embodiments previously described in relation to the coated substrate.

According to another aspect of the invention, there is provided a method for preparing a biocompatible coated substrate. In one embodiment, the method comprises providing a substrate having a surface, heating the substrate to a beginning deposition temperature, applying a calcium phosphate film to the surface of the substrate; and manipulating the deposition temperature during the applying step. According to this embodiment of the invention, there is formed a coating on the substrate comprising a calcium phosphate film having an inner layer bonded to the surface of the substrate, one or more intermediate layers, and an outer layer, wherein the film is functionally graded in at least one of crystallinity and crystal diameter such that crystallinity and crystal diameter decrease from the inner layer to the outer layer. Preferably, crystallinity and crystal diameter both decrease from the inner layer to the outer layer.

In one embodiment of the invention, the calcium phosphate coating is applied using an Ion Beam Assisted Deposition (IBAD) system. Preferably, the IBAD system comprises dual ion beam sputtering using a primary beam and an assist beam. One embodiment of a dual ion beam sputtering system is provided in FIG. 1. It is understood, however, that the present invention is not limited to a single type of sputtering system, but could rather be practiced with any number of similar systems readily understood by one of skill in the art. In the embodiment shown in FIG. 1, the primary ion source is an 8 cm Kaufman-type ion source, used for sputtering the source material from the target, and the secondary ion source is a 3 cm Kaufman-type source, used for ion bombardment.

Use of IBAD provides multiple advantages over plasma spraying. When using IBAD, the calcium phosphate film bonds to the surface of the substrate on an atomic level, which leads to better and more consistent adhesion strength than available with plasma sprayed coating. By applying the calcium phosphate coating with an IBAD system, the calcium phosphate is deposited on the surface of the substrate molecule by molecule. This allows for the formation of intermolecular bonds, in part because of the use of the assist beam, which directs the individual molecules to the surface of the substrate. Accordingly, the inner layer of the calcium phosphate film is bonded to the surface of the substrate through intermolecular bonding with the substrate molecules. Further, such intermolecular bonding can occur between the coating molecules and the substrate molecules at or beneath the surface of the substrate. The molecule by molecule deposition of the calcium phosphate coating further allows for precise control of thickness and other physical characteristics. Accordingly, use of the IBAD system for applying the calcium phosphate coating to the substrate allows for much thinner coating than can be applied using plasma spray techniques. Thinner coatings can provide a higher interfacial strength and better fracture resistance than thicker plasma spray coatings.

In one embodiment of the invention, the coating applied to the substrate has an overall thickness of about 100 nm to about 2,000 nm. Preferably, the coating has an overall thickness of about 200 nm to about 1,500 nm, more preferably about 300 nm to about 1,000 nm. Coating thickness can vary depending upon the length of time of deposition, which can be controlled within close limits. Accordingly, coatings of precisely defined thicknesses can be prepared according to the method of the invention. Further, the thickness of the individual layers within the coating can also be controlled within close limits by varying the length of time of deposition in coordination with the manipulation of the deposition temperature, as described below.

In addition to the advantages described above in relation to improving mechanical strength and bonding with the substrate, the method of the invention is further advantageous in relation to the ability to prepare coated substrates with a functionally graded coating. Accordingly, the method of the invention provides the ability to prepare coated substrates wherein the coating has a higher percentage of amorphous phase calcium phosphate near the outer surface of the coating (to achieve better osseointegration an bone formation) and a higher percentage of crystalline calcium phosphate near the interface of the coating with the substrate (to achieve better mechanical and bonding strength). The coated substrate prepared according to the method of the invention has a nano-scale grain structure that closely mimics the structure of bone itself, thereby facilitating the in-growth of bone with the coated substrate, and generally improving the success of an implanted item or device.

Preparing such a desirable functionally graded coating on a substrate is achieved through manipulation of the deposition temperature during the application of the calcium phosphate coating on the substrate. The physical state of the coating deposited on the substrate is in part a function of temperature. Accordingly, the physical state of the coating can be varied throughout the thickness of the coating by varying the temperature at the time of deposition of the coating on the substrate.

The method according to the invention can vary depending upon the nature of the material being applied. Preferably, the substrate to be coated is initially heated to a predetermined beginning deposition temperature. The beginning deposition temperature can be any temperature known to correspond to a temperature useful for depositing a material in a specific phase or state. In one embodiment, the beginning deposition temperature is a temperature known to correspond to a crystalline phase-forming temperature of the material for deposition. Accordingly, the material first deposited on the substrate will comprise a high percentage of crystalline material, such as calcium phosphate. In one preferred embodiment, the calcium phosphate applied to the substrate is hydroxyapatite. Accordingly, in one embodiment, the crystalline phase-forming temperature is in the range of about 500° C. to about 800° C. Preferably, the crystalline phase-forming temperature is in the range of about 650° C. to about 750° C.

The temperature manipulation portion of the method comprises lowering and, optionally, raising the temperature as desired throughout the deposition process to affect the phase or state of the material being deposited on the substrate to prepare a coating that is functionally graded according to desired specifications. In particular, the use of temperature manipulation in combination with an IBAD system leads to formation of coated substrates wherein the coating can be prepared within closely defined specifications, including coating thickness, composition, and phase.

In one particular embodiment of the invention, the manipulation step comprises lowering the deposition temperature. In the coating of the present invention, it is desirable to have calcium phosphate in a crystalline phase near the substrate interface and calcium phosphate in an amorphous state near the outer surface of the coating. With hydroxyapatite, for example, it is known that deposition at higher temperatures will lead to formation of a crystalline HA layer, while deposition at lower temperature will lead to formation of an amorphous HA layer. Accordingly, in one embodiment of the invention, the temperature manipulating step comprises lowering the deposition temperature to an amorphous phase-forming temperature. Such lowering can be stepwise (i.e., immediate lowering to a predetermined temperature) or can be gradual. In one embodiment of the invention, the amorphous phase-forming temperature is in the range of about 250° C. to about 500° C. As would be readily recognizable by one of skill in the art, the amorphous phase-forming temperature (as well as the crystalline phase-forming temperature) could vary depending upon the exact chemical nature of the material for deposition. Accordingly, the present invention is not limited to the specific temperature ranges provided herein, but also foresees that other temperature ranges specific to the material for deposition are also encompassed by the invention.

In one embodiment of the coating of the invention, it is beneficial to heat the substrate to a beginning deposition temperature, begin application of the calcium phosphate coating (to facilitate formation of crystalline calcium phosphate), and then lower the deposition temperature (to facilitate formation of amorphous calcium phosphate). The invention, however, also encompasses methods wherein the temperature manipulation comprises raising the temperature from the beginning deposition temperature. The invention also encompasses methods wherein the temperature manipulation comprises alternately raising and lowering the temperature through a varying number of cycles to achieve a functionally graded coating with a more complex grading. For example, if desirable, alternating layers of crystalline and amorphous HA could be applied by alternately raising and lowering the deposition temperature.

The method of the invention can further comprise manipulation of one or more of the ion beams used in the deposition process. In one particular embodiment of the invention, the IBAD system comprises a dual ion beam sputtering system comprising a primary beam and an assist beam, each set according to predetermined parameters. In one particular embodiment, the primary beam and the assist beam are each set at a predetermined voltage. The predetermined settings for the primary beam and the assist beam can vary depending upon the substrate to be coated, the coating material, and the exact desired properties of the coated substrate. One or more of the parameters of the primary beam and the assist beam can then be manipulated to further affect the nature of the coating on the substrate.

In one embodiment of the invention, the method can further comprise manipulating the assist beam, such as by lowering the voltage from the beginning voltage to a lower voltage. It is useful to begin the deposition process with the assist beam set at a higher voltage to facilitate better bonding strength at the interface of the coating with the substrate. After a new atomic layer has been deposited on the substrate, it is useful, according to one embodiment of the invention, to lower the voltage of the assist beam to avoid disruption of the newly formed coating layers. Preferably, the assist beam voltage is lowered after a specified period of time known to correspond to a time useful for deposition of a strongly bonded inner coating layer. In one embodiment of the invention, the assist beam voltage is lowered from the beginning voltage after a time of about 5 minutes to about 15 minutes.

The method of the invention, in addition to applying a calcium phosphate coating to a substrate, can also encompass the application of further materials. In one embodiment, the method further comprises application of one or more additional components useful for increasing the stability and mechanical properties of the calcium phosphate or for increasing the initial calcium absorption of the coating from serum. In one embodiment, the additional component includes yttrium.

The addition of the further components to the calcium phosphate coating of the invention can be by any method known in the art. When the coating is prepared according to the method of the invention, it is beneficial to include the additional component through doping of the target used in the IBAD system. The target generally comprises the material ultimately desired to be applied to the substrate. For example, in one embodiment of the invention, the target comprises an amount of hydroxyapatite. The target can further comprise an additional material particularly useful for holding the material to be sputtered. In a particular embodiment, the target comprises an amount of pressed hydroxyapatite held on a copper plate. Other types of backing material, or plates, can also be used, such as steel. The present invention, however, is not limited to these specific embodiments and can also comprise further materials that would be evident to one of skill in the art.

As previously noted, the additional components added to the calcium phosphate coating, while beneficial, are generally intended to be included only in a doping amount. Accordingly, it is beneficial for the method of the invention to be particularly adaptable for allowing the inclusion of a source for the one or more additional components. In one embodiment of the invention, the additional component added to the calcium phosphate coating is yttrium, and the yttrium is introduced to the coating by overlying strips of elemental yttrium on the hydroxyapatite target. For example, in one embodiment, two yttrium strips are placed in a cross pattern over the target, the strips being of a particular size such that the coating applied to the substrate exhibits the desired percentage of yttrium doping.

According to this embodiment of the invention, the percentage yttrium in the coating applied to the substrate can be determined according to the following formula:

$$Y\% = [(Y_{sa}/T_{sa}) \times (Y_{sy}/HA_{sy})] \times 100$$

wherein $Y_{sa}$ is the surface of the yttrium strips; $T_{sa}$ is the total target surface area; $Y_{sy}$ is the yttrium sputter yield; and $HA_{sy}$ is the hydroxyapatite sputter yield. Further, $Y_{sa}$ can be determined according to the following equation:

$$Y_{sa} = [(Y\% \times T_{sa} \times HA_{sy})/Y_{sy}] \times 100$$

wherein each variable is as defined above. Similarly, when other components are added to the calcium phosphate, the percentage of the component included in the final coating and surface area of the component placed on the target can be calculated according to the above equations. Therefore, the invention readily encompasses methods for including multiple different components in the coating of the invention.

The invention is particularly suited for preparing coated dental implants, coated orthopedic implants, and other types of coated prosthetics. Generally, the invention can be used in the preparation of coated substrates wherein the substrate is any of the various dental and orthopedic items previously noted. In one embodiment of the invention, there is provided a coated dental implant comprising a dentally implantable substrate having a surface that is at least partially coated with a calcium phosphate film having an inner layer bonded to the surface of the dentally implantable substrate, one or more intermediate layers, and an outer layer, wherein the film is functionally graded in crystallinity and crystal diameter such that crystallinity and crystal diameter both gradually decease from the inner layer to the outer layer. In a particular embodiment, the calcium phosphate film coating the dentally implantable substrate includes calcium phosphate selected from the group consisting of hydroxyapatite, tricalcium phosphate, and mixtures thereof. In still another embodiment, the calcium phosphate film further comprises one or more additional component, such as yttrium.

According to another embodiment of the invention, there is provided a coated orthopedic implant comprising an orthopedically implantable substrate having a surface that is at least partially coated with a calcium phosphate film having an inner layer bonded to the surface of the orthopedically implantable substrate, one or more intermediate layers, and an outer layer, wherein the film is functionally graded in crystallinity and crystal diameter such that crystallinity and crystal diameter both gradually decease from the inner layer to the outer layer. In a particular embodiment, the calcium phosphate film coating the orthopedically implantable substrate includes calcium phosphate selected from the group consisting of hydroxyapatite, tricalcium phosphate, and mixtures thereof. In still another embodiment, the calcium phosphate film further comprises one or more additional component, such as yttrium.

A functionally graded coating deposited on a substrate according to the method of the invention has been prepared and examined to study the microstructure and physiological performance thereof. Various characterization techniques, such as profilometry, transmission electron spectroscopy (TEM), scanning transmission electron microscopy (STEM), nano-indentation testing, and microscratch testing were used to analyze the coated substrates. Such preparation and analysis of the inventive coating are described more fully in the examples provided below.

EXPERIMENTAL

The present invention is more fully illustrated by the following examples, which are set forth to illustrate various embodiments of the invention and are not to be construed as limiting thereof.

Example 1

Preparation of Coated Substrate

A coated substrate was prepared by depositing a hydroxyapatite film on a silicon substrate in a dual ion beam sputtering system as shown in FIG. 1. The base pressure of the dual ion beam sputtering system was set at $9 \times 10^{-7}$ Torr. A 15.24 cm diameter hydroxyapatite target recessed into a stainless steel holder was used as the hydroxyapatite source.

For the duration of the deposition process, the primary ion source was set at 1000V, and a gas flow of 3 sccm was provided to each ion source bringing the background pressure of the system to approximately $4 \times 10^4$ Torr. The assist beam was initially set to 1000V. After 10 minutes of deposition, the assist beam was set to 400V, and it remained at that setting for the remainder of the deposition.

For the first 2 hours of deposition, the substrate heater was set at 700° C. After two hours of deposition, the substrate heater was reduced to 500° C. After an additional 2 hours, the heater was completely turned off. During the final 30 minutes of deposition, the substrate was allowed to gradually cool, the substrate temperature ultimately falling to 250° C. at the end of the deposition. Total deposition time was 4.5 hours. A summary of the deposition parameters is provided in Table 1.

TABLE 1

| Step | Time | Assist Beam Voltage | Primary Beam Voltage | Substrate Temperature |
|---|---|---|---|---|
| 1 | 1–10 minutes | 1000 V | 1000 V | 700° C. |
| 2 | 10–120 minutes | 400 V | 1000 V | 700° C. |
| 3 | 120–240 minutes | 400 V | 1000 V | 500° C. |
| 4 | 240–270 minutes | 400 V | 1000 V | 500° C.–250° C. |

Example 2

Structural Analysis of Hydroxyapatite Film on Coated Substrate

Figure 2:
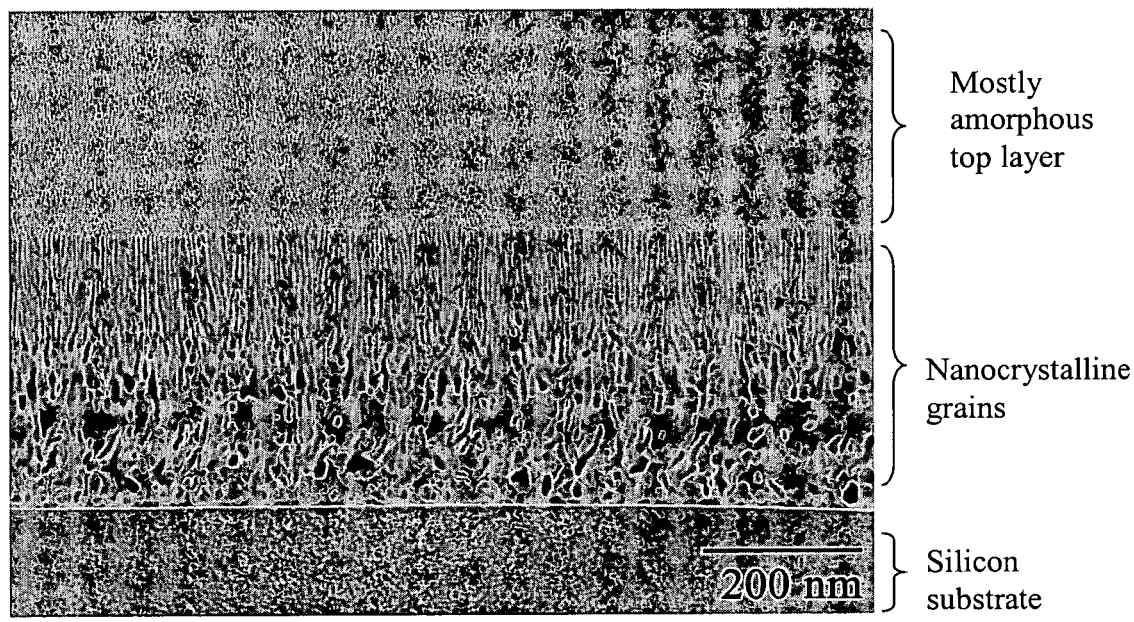
FIG. 2 is a TEM image of a cross-section of a hydroxyapatite film according to the invention coated on a silicon substrate.

The cross-sectional structure of the HA film prepared in Example 1 is shown in FIG. 2. The figure provides a TEM cross-sectional image of the functionally graded HA film. The film has an overall thickness of 875 nm, and on visual inspection, the film can be seen to include a number of distinct layers. The silicon substrate is covered by a thin amorphous layer of silicon dioxide (about 12 nm thick), followed by a coarse crystalline HA layer (210 nm thick). On top of that is a fine crystalline HA layer (140 nm thick), followed by a layer of amorphous HA mixed with very fine nano-structure HA grains (513 nm thick).

Figure 3:
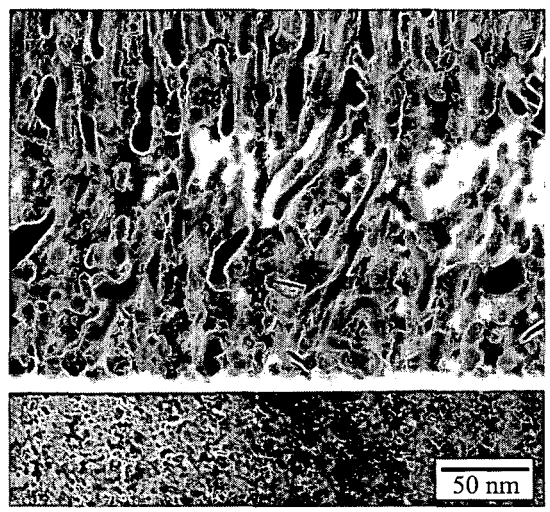
FIG. 3 is a detailed view of the TEM image of FIG. 2 showing the interfacial region between the HA coating and the silicon substrate.
Figure 4:
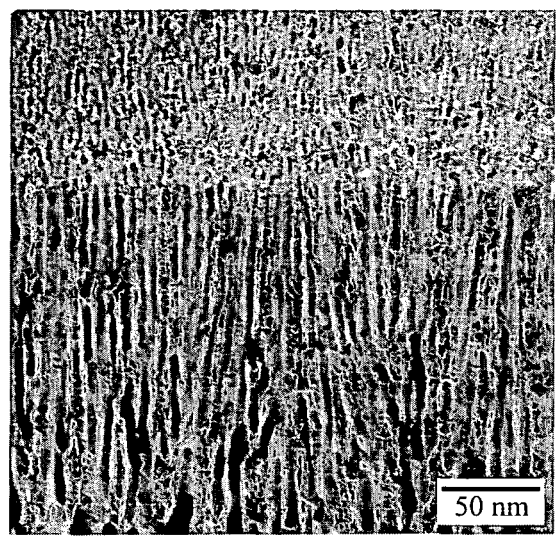
FIG. 4 is a detailed view of the TEM image of FIG. 2 showing the nano columnar HA crystals underneath the amorphous HA.

As can be seen in FIG. 2, the degree of crystallinity decreases from the bottom layer (in contact with the substrate) to the top layer. The bottom layer comprises predominately crystalline HA, while the top layer comprises predominately amorphous HA. Further, the crystal grain size also decreases from the bottom layer to the top layer. Large nano crystals are present in the bottom layer, smaller nano crystals are present in the intermediate layer, and very little crystallization is seen in the top layer. The functional grading of the coating is further seen in FIGS. 3 and 4, which provide detailed views of the interfacial region between the HA coating and the silicon substrate, and the transition between the nano columnar HA crystals and the amorphous crystals, respectively.

Figure 5:
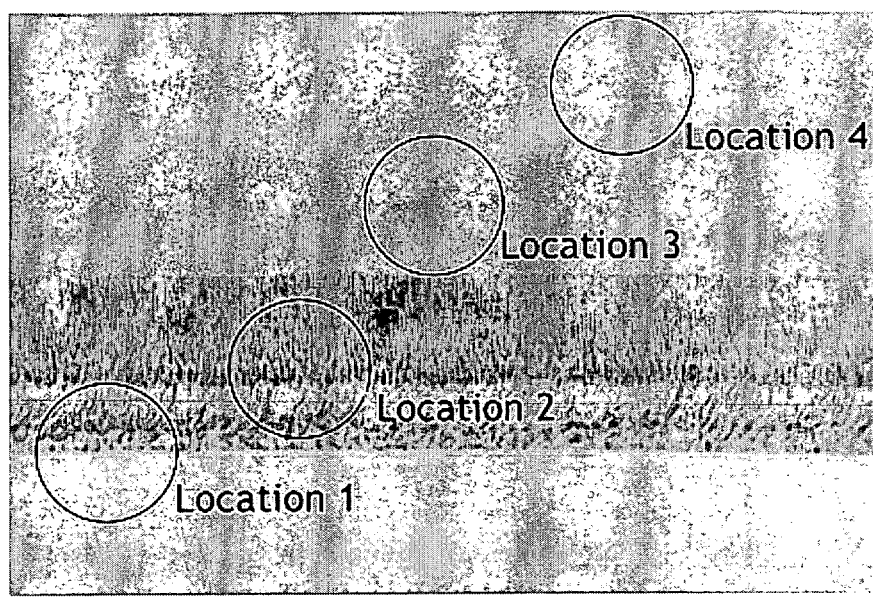
FIG. 5 is a TEM image of the cross-section of a hydroxyapatite film according to the invention marked at various areas from which SAD patterns were taken.

The selected area diffraction (SAD) patterns seen from the various layers further confirm the decreasing crystallinity of the inventive coating moving toward the top layer of the film. FIG. 5 shows a TEM image of the cross-section of the coated substrate marked at the various areas from which SAD patterns were taken. Comparison of the TEM image with the SAD patterns of locations 1-4 further illustrates the decreasing crystallinity of the film moving away from the substrate and toward the top layer of the film.

Figure 6A:
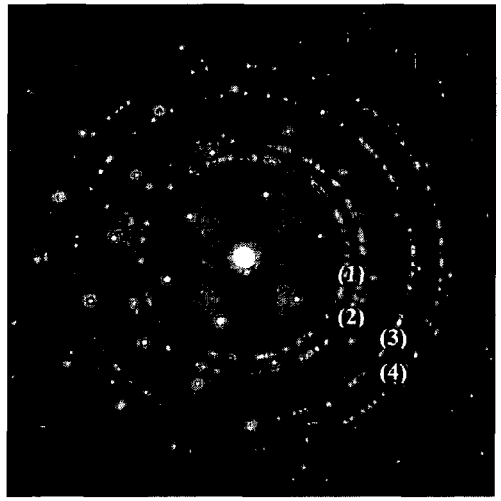
FIGS. 6a-6d are SAD patterns from areas indicated in FIG. 5 as locations 1 to 4, respectively.
Figure 6B:
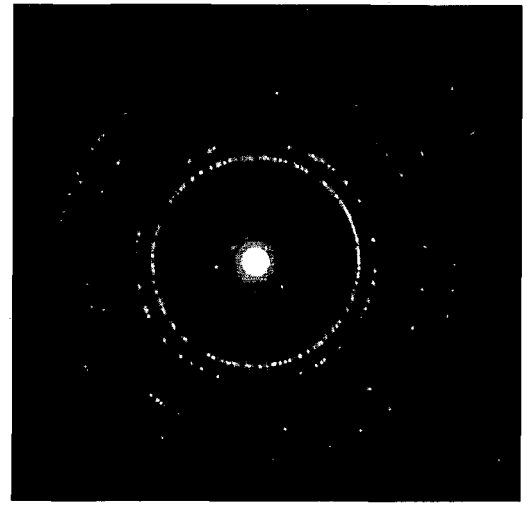
Figure 6C:
Figure 6D:

The SAD pattern from location 1, shown in FIG. 6a, is a mixture of HA film and silicon substrate. A well-defined spot pattern is visible arising from the silicon substrate with a (011) zone axis. The rings numbered 1-4 in FIG. 6a correspond to polycrystalline HA with (113), (213), (501), and (423) planes, respectively. FIG. 6b reveals a similar ring pattern indicating the presence of crystalline HA in location 2 of FIG. 5. The SAD patterns from location 3 (FIG. 6c) and location 4 (FIG. 6d) are composed of diffused rings, indicating an amorphous phase, possibly mixed with very fine nanocrystals. The distances of the diffused rings shown in location 3 and location 4 are similar with the d-spacings in location 1 and location 2, indicating the material found in location 3 and location 4 is also HA, albeit in an amorphous phase. STEM analysis from various layers of the functionally graded HA film showed a Ca/P ratio very close to 1.66, which is the ratio for pure HA.

Example 3

Preparation of Comparative Coated Substrate

For use as a comparative to the coating of the invention, a calcium phosphate film was sputtered on a cleaned glass surface using a CMS-18 radiofrequency magnetron sputtering system. The target used in the sputtering process was a 101.6 mm diameter sintered HA target on a copper backing. The base pressure in the sputtering chamber was about $6.5 \times 10^{-6}$ Torr. Sputter-deposition was performed using a process pressure of about 1.0 to about 1.5 mbar and a sputtering power of 200 W for 7 hours. A coating rate of 60 nm per hour was observed. After sputtering, the coated samples were subjected to post-deposition heat treatment at 500° C. for 30 minutes using a Thermolyne 48000 furnace to prepare a crystalline phase coating. The post-deposition heat treatment resulted in a crystallinity of 62% (+/−2%), which was confirmed by X-ray diffraction.

Example 4

Adhesion Characteristics Comparison

Adhesion characteristics were compared for the functionally graded HA film prepared in Example 1 and the sputter-deposited film of 62% crystallinity prepared as described in Example 3. Adhesion was determined using a CSM Microscratch Instrument. Scratch tests were performed under a linearly increasing load that increased from 0.01 N to 3 N. The scratch length was set to 3 mm, and the scratch speed was set to 1 mm/minute. A diamond tip (20 μm tip diameter, Rockwell C geometry) was used for the scratch testing.

Scratch testing was performed in two samples of the functionally graded HA film of the invention, as prepared in Example 1. In the first functionally graded HA film sample, the first critical load occurred at 0.30 N. At higher loads, continuous film cracking was observed. No significant spalling or external transverse cracking was observed, indicating good adhesion of the film to the substrate under the given loading conditions. The scratch tip reached the substrate in the first sample at a load of 2 N, and plastic deformation of the silicon substrate was observed at that load. In the second functionally graded HA film sample, film penetration again did not occur until a load of 2 N was achieved.

In the sputter-deposited film of 62% crystallinity prepared according to the method of Example 3, film penetration occurred at 0.42 N, which is much lower than in the functionally graded HA film of the invention (film penetration at 2 N). These test results illustrate the increased ability of the coated substrate of the invention to resist cracking.

Example 5

Nanohardness and Young's Modulus

Nanohardness and Young's modulus values for the functionally graded HA film prepared in Example 1 and the sputter-deposited film of 62% crystallinity prepared as described in Example 3 were determined using an MTS Nanoindenter II® instrument. The samples were indented with a DCM tip with a radius of curvature of 20 mm. Indentations were performed using a trapezoidal loading curve. The nanohardness and Young's modulus were measured as a function of indentation depth. The maximum load was varied between 150 mN and 600 mN. A constant loading rate of 30 mN/s was applied. The tip was calibrated following the partial unloading method, and was cleaned with isopropanol between indentations. The modulus and hardness were determined using the Oliver-Pharr model.

Table 2 provides a summary of the average hardness and average Young's modulus values for the several films at a 100 nm maximum indentation depth. As in Example 4, two samples of a hydroxyapatite coated substrate according to the invention are compared against the sputter-deposited film of 62% crystallinity described above in Example 3. As a further comparative, reported values for sintered HA are also provided [see, Kumar, R. R. and Wang, M., *Materials Science and Engineering A*338, 230-236 (2000)].

TABLE 2

| Film | Substrate | Average Hardness (GPa) | Average Young's Modulus (GPa) |
|---|---|---|---|
| Inventive Functionally Graded HA (sample 1) | Silicon | 6.472 | 132.998 |
| Inventive Functionally Graded HA (sample 2) | Silicon | 6.391 | 121.514 |
| Sputtered and Annealed HA | Glass | 5.101 | 95.892 |
| Sintered HA | NA | 6.19 | 125 |

As seen in Table 2, the functionally graded hydroxyapatite coating of the invention generally provides higher modulus and hardness values than the sputter-deposited films. Further, these values are also generally greater than the reported values for sintered hydroxyapatite.

Example 6

Cell Adhesion and Differentiation on Inventive Hydroxyapatite Coating

Initial cell adhesion and cell differentiation on the coating prepared according to Example 1 was evaluated using ATCC CRL 1486 human embryonic palatal mesenchymal cell, and osteoblasts precursor cell line. The cells were seeded on the HA coating in 6 well culture plates at a density of 50,000 cells/sample in Dubecco Modified Eagle's Medium (DMEM) and incubated.

Figure 7:
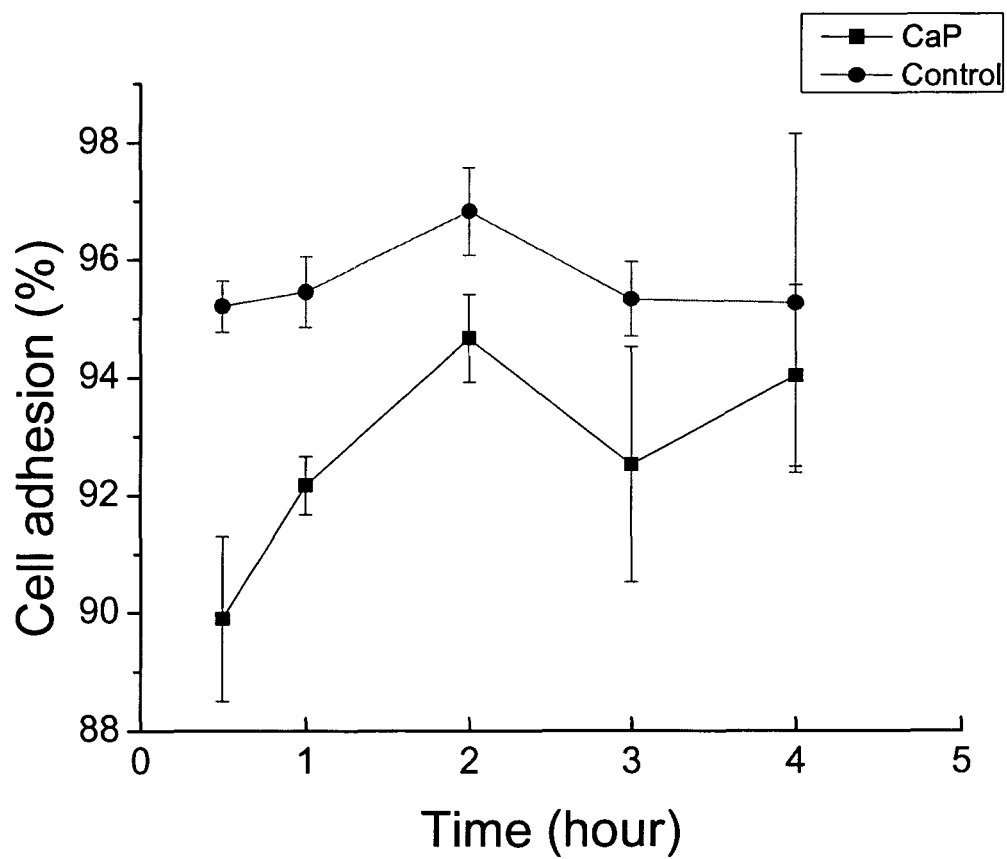
FIG. 7 is a chart illustrating percentage cell adhesion versus time for cells incubated on a hydroxyapatite coating according to one embodiment of the invention.

After 0.5, 1, 2, 3, and 4 hours of incubation, the non-adherent cells were removed and counted using a Coulter Counter. The percentage cell adhesion was calculated by the following equation:

Number of initial cells suspended−Number of non-adherent cells×100 Number of initial cells suspended FIG. 7 provides a chart of percentage cell attachment on the inventive HA coating versus time. As a comparative, the chart further provides the percentage cell attachment on a silicone surface. On the inventive HA coating, optimal adhered cell concentration was observed after 2 hours incubation. On the silicone surface, optimal adhered cell concentration was observed after 0.5 hours incubation.

Cell layer protein synthesis and alkaline phosphatase specific activity were also measured at 4 days after cell confluence. Protein synthesis was performed using the Pierce BCA protein assay. After 4 days incubation, the protein production by cells cultured on the inventive HA coating was 0.0004 μg/μl (+/−0.0001). In comparison, protein production by cells cultured on the silicone control surface was 0.0005 μg/μl (+/−0.0002).

Alkaline phosphatase (ALP) production was determined from p-nitrophenol stock standard. The ALP specific activity (nmol ALP/g protein) was calculated by normalizing ALP production to the total protein produced. After 4 days incubation, the ALP specific activity on the inventive HA coating was 2.00 nmol/μg (+/−0.69). In comparison, the ALP specific activity on the silicone control surface was 0.13 nmol/μg (+/−0.21).

As seen from the above data, cell adhesion on the inventive HA coating reached a plateau, and remained there, after 2 hours incubation, indicating good cell adhesion on the HA coating. Further, the cells on the HA coating exhibited significantly less total protein production compared to the control, but also produced significantly greater alkaline phosphatase specific activity as compared to the control (p=0.00042). These results indicate that the inventive HA coating enhances osteoblast differentiation.

Many modifications and other embodiments of the invention will come to mind to one skilled in the art to which this invention pertains having the benefit of the teachings presented in the foregoing descriptions and associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A biocompatible coating comprising a layer of a calcium phosphate film having a top and a bottom and having a defined thickness of about 100 nm to about 2,000 nm, wherein, at the bottom of the layer, the calcium phosphate is predominately crystalline and has a crystal diameter of up to about 50 nm, and wherein said layer of said film is functionally graded in crystallinity and crystal diameter such that crystallinity and crystal diameter each gradually reduces across the thickness of said layer such that, at the top of the layer, the calcium phosphate is at least about 75% amorphous and any crystalline calcium phosphate has a crystal diameter of less than about 10 nm.

2. The biocompatible coating of claim 1, wherein said calcium phosphate is selected from the group consisting of hydroxyapatite, tricalcium phosphate, and mixtures thereof.

3. The biocompatible coating of claim 1, wherein the crystal diameter of any crystalline calcium phosphate gradually reduces from the bottom to the top of the film from a diameter of about 50 nm to a diameter of about 2 nm.

4. The biocompatible coating of claim 1, wherein said layer further comprises one or more additional component in addition to said calcium phosphate.

5. A dental implant comprising:
a dentally implantable substrate having a surface, and
a biocompatible coating according to claim 1 bonded to the surface of the dentally implantable substrate.

6. An orthopedic implant comprising:
an orthopedically implantable substrate having a surface, and
a biocompatible coating according to claim 1 bonded to the surface of the orthopedically implantable substrate.

7. A biocompatible coated substrate comprising: a substrate having a surface; and
a biocompatible coating bonded to the substrate surface and comprising a layer of a calcium phosphate film having a top and bottom and having a defined thickness of about 100 nm to about 2,000 nm, wherein, at the bottom of the layer, the calcium phosphate is predominately crystalline and has a crystal diameter of up to about 50 nm and wherein said layer of said film is functionally graded in crystallinity and crystal diameter such that crystallinity and crystal diameter each gradually reduces across the thickness of said layer such that, at the top of the layer, the calcium phosphate is at least about 75% amorphous and any crystalline calcium phosphate has a crystal diameter of less than about 10 nm.

8. The coated substrate of claim 7, wherein said substrate is a prosthetic implant.

9. The coated substrate of claim 8, wherein said prosthetic implant is selected from the group consisting of a dental implant and an orthopedic implant.

10. The coated substrate of claim 7, wherein said substrate comprises one or more metallic material.

11. The coated substrate of claim 10, wherein said substrate comprises a material selected from the group consisting of titanium, titanium alloys, cobalt/chromium alloys, steel, and mixtures thereof.

12. The coated substrate of claim 7, wherein said layer of said calcium phosphate film has a thickness of about 100 nm to about 2,000 nm.

13. The coated substrate of claim 12, wherein said layer of said calcium phosphate film has a thickness of about 200 nm to about 1,500 nm.

14. The coated substrate of claim 12, wherein said layer of said calcium phosphate film has a thickness of about 300 nm to about 1,000 nm.

15. The coated substrate of claim 7, wherein said calcium phosphate is selected from the group consisting of hydroxyapatite, tricalcium phosphate, and mixtures thereof.

16. The coated substrate of claim 7, wherein said layer of said film comprises a portion of crystalline calcium phosphate having crystals with a diameter in the range of about 2 nm to about 50 nm.

17. The coated substrate of claim 7, wherein said layer of said film comprise a mixture of crystalline calcium phosphate and amorphous calcium phosphate.

18. The coated substrate of claim 7, wherein said layer of said film is bonded to said surface of said substrate through intermolecular bonding with substrate molecules at or beneath the surface of the substrate.

19. The coated substrate of claim 7, wherein said film further comprises one or more additional component in addition to said calcium phosphate.

20. The biocompatible coating of claim 4, wherein the additional component is yttrium.

* * * * *